(12) United States Patent
Kwon et al.

(10) Patent No.: US 7,511,023 B2
(45) Date of Patent: Mar. 31, 2009

(54) ANTICANCER DRUG-CHITOSAN COMPLEX FORMING SELF-AGGREGATES AND PREPARATION METHOD THEREOF

(75) Inventors: Ick Chan Kwon, Seoul (KR); In-San Kim, Daegu (KR); Seo Young Jeong, Kyunggi (KR); Hesson Chung, Incheon (KR); Yong Woo Cho, Seoul (KR); Yoen Ju Son, Seoul (KR); Chong Rae Park, Seoul (KR); Sang Bong Seo, Kyunggi (KR)

(73) Assignee: Korea Institute of Science and Technology, Seoul (KR)

( * ) Notice: Subject to any disclaimer, the term of this patent is extended or adjusted under 35 U.S.C. 154(b) by 481 days.

(21) Appl. No.: 10/473,629

(22) PCT Filed: Aug. 14, 2002

(86) PCT No.: PCT/KR02/01554

§ 371 (c)(1),
(2), (4) Date: Oct. 1, 2003

(87) PCT Pub. No.: WO03/015827

PCT Pub. Date: Feb. 27, 2003

(65) Prior Publication Data

US 2004/0138152 A1     Jul. 15, 2004

(30) Foreign Application Priority Data

Aug. 18, 2001   (KR) ................................ 2001-49772

(51) Int. Cl.
*A01N 43/04* (2006.01)
*A61K 31/70* (2006.01)
(52) U.S. Cl. .......................................... 514/34; 514/55
(58) Field of Classification Search .................. 514/34, 514/55
See application file for complete search history.

(56) References Cited

U.S. PATENT DOCUMENTS

| 5,208,020 | A | * | 5/1993 | Chari et al. | .............. | 424/181.1 |
| 5,306,809 | A | * | 4/1994 | Boon et al. | ................. | 530/363 |
| 6,730,735 | B2 | * | 5/2004 | Davis et al. | ................. | 525/54.2 |

FOREIGN PATENT DOCUMENTS

| EP | 398305 A2 | 11/1990 |
| JP | 01-061429 A2 | 8/1989 |
| JP | 01252603 | * 10/1989 |
| JP | 401252605 A | * 10/1989 |
| WO | WO 97/41894 | * 11/1997 |
| WO | WO99/22739 | 5/1999 |

OTHER PUBLICATIONS

Miwa et al., "Development of Novel Chitosan Derivatives as Micellar Carriers of Taxol", Pharmaceutical Research, vol. 15, No. 12, 1998, pp. 1844-1850.*
Miwa et al., "Development of Novel Chitosan Derivatives as Micellar Cariers of Taxol", Pharmaceutical Research, vol. 15, No. 12, pp. 1844-1850, 1998.*
Son et al., "Synthesis of Adriamycin-conjugated Glycol Chitosan and In Situ Self-Association", Polymer Preprints, 2001, 42(2), 129-130.*
Ouchi et al. ("Design of Chitin or Chitosan/5-Fluorouracil conjugate having antitumor activity", Advanced Chitin/Chitosan (Proc Int Conf—meeting date 1991), vol. 5, 1992, pp. 106-115).*
Sato et al., "Preparation and drug release characteristics of the conjugates of mitomycin C with glycol-chitosan and N-succinyl-chitosan", Biol. Pharm. Bull. 1996, 19(2), abstract.*
Miwa et al., "Development of novel chitosan derivatives as micellar carriers of taxol," Pharmaceutical Research 1998; 15(12): 1844-1850.
International Search Report for PCT Application No. PCT/KR02/01554, issued by the Korean Intellectual Property Office on Oct. 30, 2002.
Schatzlein et al., "Chitosan based polymeric vesicles as anti-cancer drug carriers," Proceedings of the International Symposium on Controlled Release of Bioactive Materials 1998; 25th; 435-436.
Ouchi, Tatsuro, Banba, Toshio, Masuda, Hiroshi. *Design of Chitosan-5FU Conjugate Exhibiting Antitumor Activity*, J. Macromol. Sci.—Chem.1 A28(10), pp. 959-975 (1991).
Schatzlein, A.G., Sludden, J., Tetley L., Mosha, E., Uchegbu I.F. *Chitosan Based Polymeric Vesicles as Anti-Cancer Drug Carriers*, Proceed. Int'l. Symp. Control. Rel. Bioact. Mater., 25 (1998) Controlled Release Society, Inc. pp. 435-436.

* cited by examiner

*Primary Examiner*—Traviss C McIntosh, III
(74) *Attorney, Agent, or Firm*—Lucas & Mercanti, LLP

(57) ABSTRACT

The present invention relates to an anticancer drug-chitosan complex forming self-aggregates and the preparation method thereof. More precisely, the present invention relates to the anticancer drug-chitosan complex forming self-aggregates in aqueous media composed of a hydrophobic anticancer agent and a hydrophilic chitosan, and the preparation method thereof. The anticancer drug-chitosan complex of the present invention not only works selectively against target tumor tissue but also continues to release the medicine over a long period of time. Besides, the anticancer drug-chitosan complex could have greater amount of drug by adding the anticancer drug into self-aggregates, which is generally limited by chemical bond. Therefore, the anticancer drug-chitosan complex of the present invention can be effectively used for the cancer chemotherapy.

7 Claims, 3 Drawing Sheets

Figures

ANTICANCER DRUG-CHITOSAN COMPLEX FORMING SELF-AGGREGATES AND PREPARATION METHOD THEREOF

FIELD OF THE INVENTION

The present invention relates to an anticancer drug-chitosan complex forming self-aggregates and the preparation method thereof. More precisely, the present invention relates to the anticancer drug-chitosan complex forming self-aggregates in aqueous media composed of a hydrophobic anticancer agent and a hydrophilic chitosan, and the preparation method thereof. The anticancer drug-chitosan complex of the present invention not only works selectively against target tumor tissue but also continues to release the medicine over a long period of time. Besides, the anticancer drug-chitosan complex could have greater amount of drug by adding the anticancer drug into self-aggregates, which is generally limited by chemical bond. Therefore, the anticancer drug-chitosan complex of the present invention can be effectively used for the cancer chemotherapy.

BACKGROUND

Anticancer chemotherapy was set about progressing as choriocarcinoma was cured completely by using methotrexate. As of today, about 50 different kinds of anticancer drugs have been used and especially, choriocarcinoma, leukemia, Wilms' tumor, Ewing's sarcoma, rhabdomyoma, retinoblastoma, lymphoma, mycosis fungoides, testis tumor et cetera have been satisfactorily treated with those anticancer drugs.

Recently, knowledge about the development of cancer and the characteristics of tumor cells has been disclosed a lot and studies concerning the development of new anticancer drugs have followed. Most anticancer drugs show anticancer effect by suppressing the synthesis of nucleic acid of tumor cells or defunctioning the nucleic acid by directly combining with the nucleic acid. However, they have serious side effects such as bone marrow depression, gastrointestinal damage and lose hair since these anticancer drugs work not only tumor cells but also for normal cells.

The biggest problem of using anticancer drugs is that those drugs do not selectively work for only tumor cells. That is; anticancer drugs are working for every cells showing fast division or proliferation (bone marrow cells, epitherial cells of stomach and intestines, hair follicle cells, etc.), causing almost every cancer patients to be suffering from side effects such as bone marrow depression, gastrointestinal trouble, and lose hair, etc. Nevertheless, the anticancer drugs have therapeutic effect against cancer because tumor cells respond more sensitively than normal cells, so that more tumor cells are destroyed than normal cells, in addition, normal cells are regenerated faster than tumor cells. Meanwhile, besides the anticancer effect, those anticancer drugs also have anti-immune effect. Thus, it is another use of anticancer drugs to be provided to patients who need organ transplantation for the purpose of eliminating rejection symptoms after transplantation. But the danger of infection should be considered for cancer patients since those drugs drop immunity.

About 50 anticancer drugs have been widely used so far. These drugs are classified according to their reaction mechanism and components. Among them, adriamycin, commonly called doxorubicin, is highly effective for the treatment of malignant lymphoma, acute myeloid leukemia, soft tissue osteosarcoma, breast cancer, ovarian cancer, lung cancer, bronchial cancer, bladder cancer, digestive system cancer, etc. Although it is a very effective anticancer drug, it still presents such side effects as severe bone marrow depression, hypofunction of heart and kidney, and outflow of blood from blood vessels into tissues (*N. Eng. J. Med.,* 1981, 305, 139).

Cancer chemotherapy is very limited because of the toxic side effects of anticancer drugs. As explained above, side effects results from the fact that the anticancer drugs used in chemotherapy lack efficient selectivity for tumor cells. To suppress the toxic side effects of the anticancer drugs to normal cells and to improve their efficiency toward malignant cells, lots of studies have been carried out. The preferable methods are using micelle or microsphere as a carrier of anticancer drug and conjugating anticancer drugs to polymeric carriers.

The first method that uses micelle or microsphere as a carrier of anticancer drug is to reduce side effects of cancer treatment by inserting anticancer drug into micelle or microsphere and letting it release slowly. When anticancer drug is administered separately, it works in a short period in large quantities, by which side effects are caused. This method is a good try to reduce those side effects by inducing slow release of the anticancer drug under the condition of enveloped in micelle or microsphere (*Pharm. Res.,* 1983, 15, 1844).

The second method is to produce anticancer drug-polymer complex by combining the drug with polymer. Side effects are caused from the fact that the anticancer drugs used in the present cancer chemotherapy lack efficient selectivity for tumor cells. Thus, studies of conjugating anticancer drugs to polymeric carriers have been carried out as one promising approach to suppress the side effects of the anticancer drugs to normal cells and to improve their efficiency toward tumor cells. Expected advantageous features of this method are preferable tissue distribution of drug given by the character of the polymeric carrier, prolonged half-life of drug. in plasma, and controlled drug release from the polymeric carrier by adjustment of the chemical properties of the bond between the drug and the carrier.

Several kinds of polymers, naturally occurring and synthetic polymers have been studied as carriers of anticancer drugs. Among naturally occurring polymers, immunoglobulins are most widely used as the carrier due to their high specificity and wide applicability to many kinds of tumor cells. Utility of immunoglobuline as the polymeric carrier is, however, restricted by its chemical and physical properties. For example, modification of immunoglobulins by anticancer drugs often leads to precipitation due to hydrophobicity of the drugs. Furthermore, modification procedures are limited to ones performed in mild conditions to avoid denaturation of the immunoglobulins during modification.

Recently, the polymeric carrier of the drug can be freely designed using many kinds of synthetic polymers available today, and various organic reactions can be used to introduce drug to the synthetic polymeric carrier. From this point of view, several kinds of synthetic polymers have been investigated, such as poly(N-2-(hydroxypropyl)methacrylamide), poly(divinyl ether-co-maleic anhydride), poly(styrene-co-maleic anhydride), dextran, poly(ethylene glycol), poly(L-glutamic acid), poly(aspartic acid) and poly(L-lysine).

Using pathophysiological characteristics of tumor tissues with anticancer drug-polymer complex, cancer can be treated. Generally in tumor tissues, more blood vessels are generated than in normal tissues in order to get enough nutrition for the growth of tumor cells. The blood vessels in tumor tissues have bigger size than those in normal tissues but their structure is defective. Drainage through a lymphatic duct is also very limited comparing normal tissues. Therefore, polymers easily permeate into tumor tissues but hardly be excreted from tumor tissues. This specific phenomenon showed in tumor tissues is called enhanced permeability and retention (EPR) effect (*Adv. Drug Deliv. Rev.,* 2000, 65, 271). As one of the treatments using anticancer drug-polymer complex, the attempt using N-(hygroxypropyl)methacrylamide (HPMA)-anticancer drug complex is under the phase II clinical trial (U.S. Pat. No. 5,037,883 (1991)).

The anticancer drug-polymer complex forming self-aggregates is expected to have a large diameter, as compared with unbound drug, which is a small molecule. The polymeric drug having ideal diameter is expected to circulate in the blood stream without embolization at capillaries, to escape from excretion in kidney, and to permeate into the target cells through blood vessels. And this self-aggregates form is expected to help protect the conjugated drug from enzymatic attack in plasma by concealing the conjugated drug with the polymer.

As a precursor of chitosan, chitin is a natural polymer comprising (1→4)-β-glycoside bond in which N-acetyl-D-glucosamine units are repeated and is generally found in outer coat of insects including invertebrate Crustacea and cell wall of fungi. Chitosan is a basic polysaccharide generated through N-deacethylation by treating chitin with the high concentration of alkali. Chitosan has been known to be superior to other synthetic polymers in cell adsorption capacity, biocompatibility, biodegradability and plasticity.

Thus, the present inventors have synthesized a novel anticancer drug-chitosan complex having strong points of micelle by making anticancer drug react with a polymer directly to form self-aggregates and making the anticancer drug be induced therein, which is different from the way of inserting anticancer drug into micelle. And, the present invention has been accomplished by confirming that the anticancer drug-chitosan complex can release the drug slowly and continuously, and can be controlled drug release by adjustment of the chemical properties of the bond between the drug and the chitosan, resulting in high selectivity against tumor tissues.

SUMMARY OF THE INVENTION

It is an object of the present invention to provide an anticancer drug-chitosan complex forming self-aggregates, which can be effectively used for cancer chemotherapy by releasing the drug continuously for a long period of time, by enhancing specificity against tumor tissues and by increasing the content of anticancer drug, and the preparation method thereof.

BRIEF DESCRIPTION OF THE DRAWINGS

The application of the preferred embodiments of the present invention is best understood with reference to the accompanying drawings, wherein.

A: $5 \times 10^4$ magnification (Bar: 200 nm),

B: $1 \times 10^6$ magnification (Bar: 50 nm)

Figure 3:
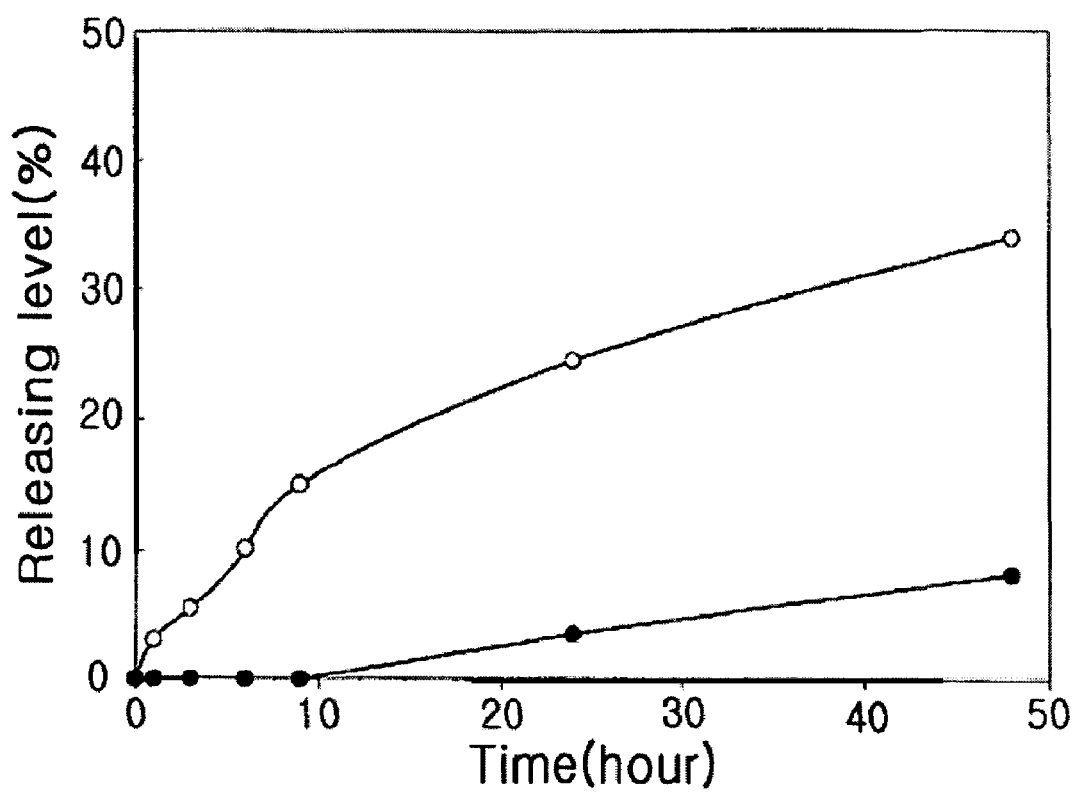

FIG. 3 is a graph showing the different releasing level of adriamycin according to the pH from the adriamycin-chitosan complex of the present invention.

0: pH 4, ● pH 7

DETAILED DESCRIPTION OF PREFERRED EMBODIMENTS

The present invention provides an anticancer drug-chitosan complex forming self-aggregates.

The present invention also provides a preparation method of the above anticancer drug-chitosan complex.

Hereinafter, the present invention is described in detail.

The present invention provides an anticancer drug-chitosan complex forming self-aggregates.

In the preferred embodiments of the present invention, every kinds of chitosan having $10^3$-$10^6$ MW can be used as a carrier of anticancer drug, and soluble chitosan having high biodegradability and biocompatibility is preferred. Especially, glycol chitosan with enhanced solubility by introducing glycol group is more preferred. And, most hydrophobic anticancer drugs can be used for the anticancer drug-chitosan complex of the present invention, and especially, adriamycin is preferred. The preferable size of the anticancer drug-chitosan complex of the present invention is 1 nm-2,000 nm. Especially, 10 nm-80 nm is more preferred.

The anticancer drug-chitosan complex of the present invention probably includes a linker additionally dissolved in an acidic condition. As a linker, cis-aconitic anhydride, glutaric anhydride, succinic anhydride, oligopeptide and benzoyl hydrazone are can be used, and especially, pH-sensitive cis-aconitic anhydride is preferred (*Biochem. Biophys. Res. Comm.,* 1981, 102, 1048).

The anticancer drug-chitosan complex of the present invention is forming micelle-like, round-shaped self-aggregates in aqueous media due to the amphiphilicity of the complex by the hydrophobic group of anticancer drug and the hydrophilic group of chitosan.

The size of anticancer drug-chitosan complex of the present invention varies according to the amount of included anticancer drug and the possible amount of included anticancer drug is 1-70 weight %.

The present inventors used the above anticancer drug-chitosan complex as an anticancer drug carrier, which include the drug forcefully therein. In the preferred embodiment of the present invention, every kind of hydrophobic anticancer drugs can be used as an anticancer drug. Especially, adriamycin, taxol, cis-platin, mitomycin-C, daunomycin and 5-fluorouracil are more preferred. The preferable diameter of anticancer drug-chitosan complex containing anticancer drug inside is 1 nm-2,000 nm, and the range between 10 nm and 800 nm is more preferred.

Inside of anticancer drug-chitosan complex of the present invention is composed of hydrophobic anticancer drug and especially some hydrophilic parts of the anticancer drug are combined with chitosan, which cause strong hydrophobicity inside of the complex. Therefore, anticancer drug-chitosan complex of the present invention provides easy access for hydrophobic anticancer drug to the inside of the complex and could increase the amount of the drug. Either the same anticancer drugs can be used for both composing anticancer drug-chitosan complex and being inserted inside of the complex. And also, many different kinds of anticancer drugs can be inserted in anticancer drug-chitosan complex all together. Owing to the similarity of properties between anticancer drug-chitosan complex composing material and inserted anticancer drug therein, this complex has greater effect as a carrier than any other carrier has.

The anticancer drug-chitosan complex of the present invention has high selectivity against tumor tissues with enhanced permeability and retention (EPR) effect, so that it can be accumulated in tumor tissues with greater amount to effectively work for target cells, comparing to small molecular weight anticancer drugs. The complex is also forming micelle-like round-shaped self-aggregates in aqueous media, which is caused by hydrophobic anticancer drug combined with hydrophilic chitosan used as a major chain. Generally, micelle is a round-shaped aggregate formed by molecules having both hydrophobic group and hydrophilic group in aqueous media. At this time, hydrophilic group is aggregating outside the formed aggregate and hydrophobic group is gathering inside (*Adv. Drug Deliv. Rev.,* 1996, 21, 107). This aggregate has been widely used as an carrier of various hydrophobic anticancer drugs. This kind of drug delivery system using amphiphilic polymer forming self-aggregates showed high selectivity against target cells and remarkably reduced cytotoxicity to normal cells. In addition, this system makes the drug be retained long enough and be released slowly and continuously resulting in an effective use for the treatment of serious disease like cancer.

The anticancer drug-chitosan complex of the present invention is an anticancer drug-polymer complex and an anticancer drug carrier having high selectivity against tumor tissues, having various advantages of micelle, and having capacity to release the drug continuously. Therefore, the anticancer drug-chitosan complex of the present invention can be effectively used as an anticancer drug having a strong anticancer effect.

The present invention also provides a preparation method of the above anticancer drug-chitosan complex.

The preparation method of the anticancer drug-chitosan complex of the present invention comprises following steps:

(1) combining hydrophobic anticancer drug with linker characterized by being dissolved in acidic condition; and
(2) combining the complex of anticancer drug and linker with hydrophilic chitosan.

In the preferred embodiment of the present invention, adriamycin is used as hydrophobic anticancer drugs. As a linker, cis-aconitic anhydride, glutaric anhydride, succinic anhydride, oligopeptide and benzoyl hydrazone are can be used, and especially, pH-sensitive cis-aconitic anhydride is preferred (*Biochem. Biophys. Res. Comm.,* 1981, 102, 1048).

Cis-aconitic anhydride used for the combining anticancer drug with chitosan is a linker which is cut in acidic pH condition and release the anticancer drug. Tumor tissues show lower pH than normal tissues. Thus, this pH-sensitive cis-aconitic anhydride can improve the selectivity of anticancer drug against tumor tissues, and relieve the cytotoxicity to normal tissues, which has been the biggest problem of anticancer drugs.

As a hydrophilic chitosan, glycol chitosan wherein glycol group is introduced is preferred.

The anticancer drug-chitosan complex of the present invention can be prepared by directly combining anticancer drug with chitosan or by linking anticancer drug to chitosan using a linker; the later is preferred.

The preparation method of anticancer drug-chitosan complex of the present invention includes the loading procedure of the anticancer drug into the inside of anticancer drug-chitosan complex forming self-aggregates.

Adriamycin, taxol, cis-platin, mytomycin-C, daunomycin and 5-fluorouracil are the examples of anticancer drug to be loaded into the inside of anticancer drug-chitosan complex.

Loading by chemical bonding is limited to 10% at best, however, by the physical loading, the loading quantity of anticancer drug can be enhanced up to 60%, resulting in the increase of anticancer drug contents over the limitation of chemical bonding.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Adriamycin-Chitosan Complex 1

<1-1> Preparation of cis-aconityl adriamycin

In order to prepare cis-aconityl adriamycin, the present inventors dissolved 13.46 mg of cis-aconitic anhydride (Chemical Formula 2) in 0.5 ml of dioxane and then dissolved 10 mg of adriamycin (Chemical Formula 1) in 350 μl of pyridine. After then, the present inventors added the cis-aconityl solution into adriamycin solution and let it be reacted at 4° C. or 24 hours.

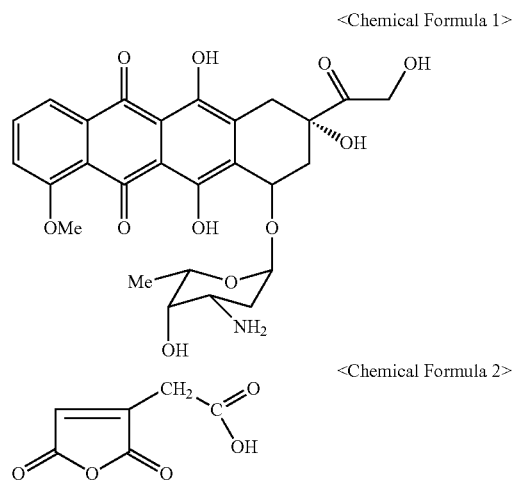

<Chemical Formula 1>

<Chemical Formula 2>

The above reaction mixture was scattered into 5 ml of chloroform and 5% NaHCO₃ solution, and stirred strongly. Then, chloroform layer in the bottom was removed and the rest solution was extracted with ethyl acetate, after which solvent was evaporated, resulting in the preparation of cis-aconityl adriamycin. The reaction procedure is summarized in the <Reaction Formula 1>.

<Reaction Formula 1>

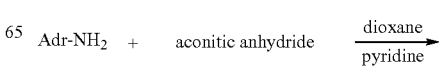

-continued

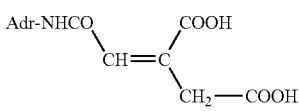

(N-cis-aconityl-adriamycin, Aco-adr)

<1-2> Preparation of chitosan complex

Figure 1:
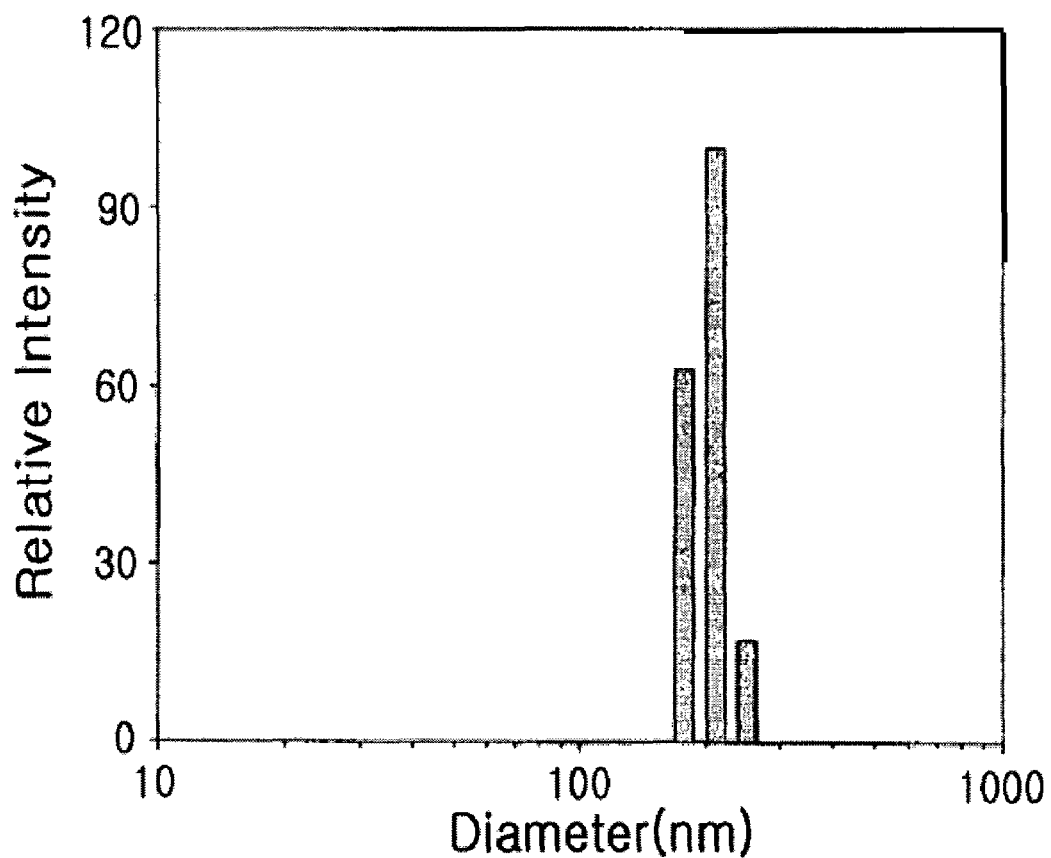
FIG. 1 is a graph showing the mean diameter and size distribution of adriamycin-chitosan complex of the present invention in aqueous solution measured by light scattering.
Figure 2:
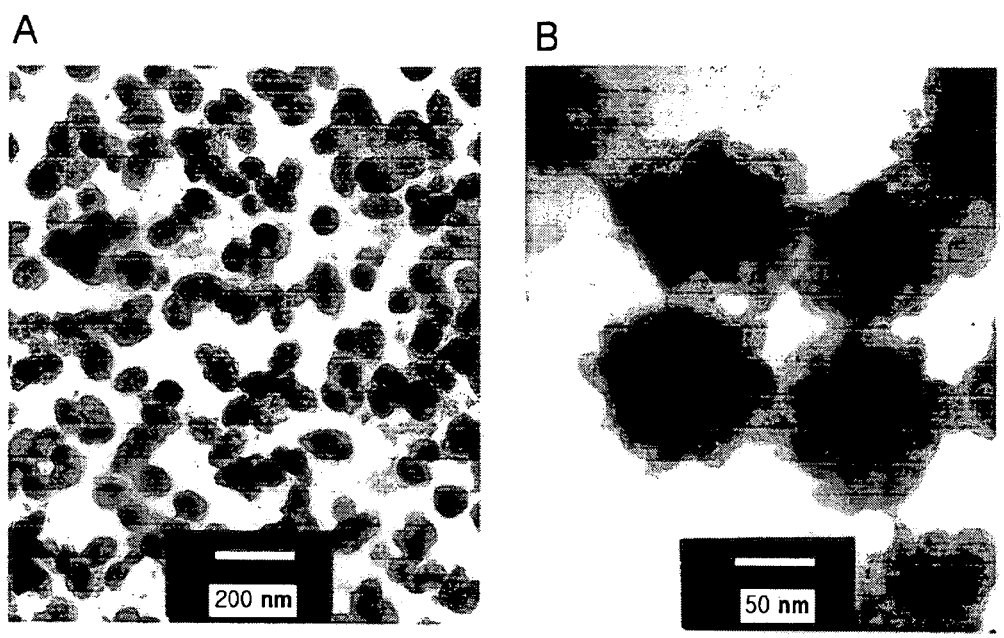
FIG. 2 is a set of transmission electron microscopy photographs of the adriamycin-chitosan complex of the present invention.

Glycol chitosan was dissolved in 10 ml of water at the concentration of 1 W % and then 10 ml of methanol was added thereto. 3 mg of cis-aconityl adriamycin was dissolved in 1 ml of DMF, which was slowly loaded into glycol chitosan solution. 7 mg of 1-ethyl-3-(3-dimethyl-aminopropyl) carbodiimide (EDC) and 5 mg of N-hydrosuccinimide (NHS) were dissolved in 1 ml of methanol, which was added into the reaction mixture and stirred at room temperature for 24 hours. The reaction mixture was dialyzed for 2 days to remove the unreacted cis-aconityl adriamycin and then freeze-dried, resulting in the preparation of adriamycin-chitosan complex of the present invention (FIGS. 1 and 2). The above reaction procedure was summarized in the following <Reaction Formula 2>.

<Reaction Formula 2>

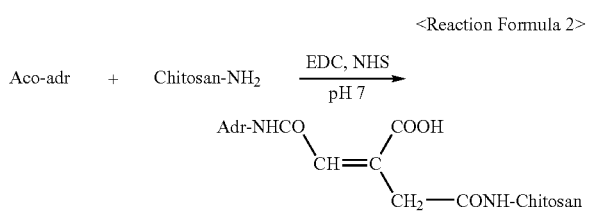

Example 2

Preparation of adriamycin-chitosan Complex 2

During the reaction process between cis-aconityl adriamycin and glycol chitosan, 2 mg of cis-aconityl adriamycin was dissolved in 1 ml of DMF, which was slowly loaded into glycol chitosan solution. After then, 4.6 mg of EDC and 3.3 mg of NHS were dissolved in 1 ml of methanol, which was added into the above reaction mixture. The same method as the above <1-2> was performed for the rest of the procedure to prepare adriamycin-chitosan complex of the present invention.

Example 3

Preparation of adriamycin-chitosan Complex 3

During the reaction process between cis-aconityl adriamycin and glycol chitosan, 1 mg of cis-aconityl adriamycin was dissolved in 1 ml of DMF, which was slowly loaded into glycol chitosan solution. After then, 2.3 mg of EDC and 1.7 mg of NHS were dissolved in 1 ml of methanol, which was added into the above reaction mixture. The same method as the above <1-2> was performed for the rest of the procedure to prepare adriamycin-chitosan complex of the present invention.

Example 4

Preparation of adriamycin-chitosan Complex 4

During the reaction process between cis-aconityl adriamycin and glycol chitosan, 4 mg of cis-aconityl adriamycin was dissolved in 1 ml of DMF, which was slowly loaded into glycol chitosan solution. After then, 9.3 mg of EDC and 6.7 mg of NHS were dissolved in 1 ml of methanol, which was added into the above reaction mixture. The same method as the above <1-2> was performed for the rest of the procedure to prepare adriamycin-chitosan complex of the present invention.

Example 5

Preparation of adriamycin-chitosan Complex 5

During the reaction process between cis-aconityl adriamycin and glycol chitosan, 5 mg of cis-aconityl adriamycin was dissolved in 1 ml of DMF, which was slowly loaded into glycol chitosan solution. After then, 11.7 mg of EDC and 8.3 mg of NHS were dissolved in 1 ml of methanol, which was added into the above reaction mixture. The same method as the above <1-2> was performed for the rest of the procedure to prepare adriamycin-chitosan complex of the present invention.

As shown in the above Example 1-Example 5, the amount of adriamycin contained in adriamycin-chitosan complex depends on the amount of cis-aconityl adriamycin.

Example 6

Preparation of adriamycin-chitosan Complex 6

Cis-aconityl adriamycin and glycol chitosan were reacted for 6 hours. And, the same method as the above <1-2> was performed for the rest of the procedure to prepare adriamycin-chitosan complex of the present invention.

Example 7

Preparation of adriamycin-chitosan Complex 7

Cis-aconityl adriamycin and glycol chitosan were reacted for 12 hours. And, the same method as the above <1-2> was performed for the rest of the procedure to prepare adriamycin-chitosan complex of the present invention.

Example 8

Preparation of adriamycin-chitosan Complex 8

Cis-aconityl adriamycin and glycol chitosan were reacted for 18 hours. And, the same method as the above <1-2> was performed for the rest of the procedure to prepare adriamycin-chitosan complex of the present invention.

Example 9

Preparation of adriamycin-chitosan Complex 9

Cis-aconityl adriamycin and glycol chitosan were reacted for 48 hours. And, the same method as the above <1-2> was performed for the rest of the procedure to prepare adriamycin-chitosan complex of the present invention.

As shown in the above Example 6-Example 9, the amount of adriamycin contained in adriamycin-chitosan complex depends on the reaction time between cis-aconityl adriamycin and glycol chitosan.

Example 10

Preparation of adriamycin-chitosan Complex Forming Self-Aggregates Containing adriamycin Therein 1

In order to prepare adriamycin-chitosan complex forming self-aggregates containing adriamycin inside, the present inventors dissolved 1 mg of adriamycin in 1 ml chloroform solution and then added triethylamine thereto. 5 mg of adriamycin-chitosan complex of the present invention was dissolved in 10 ml of water, and then the above adriamycin solution was slowed loaded thereto, followed by 24 hours stirring. At this time, let the vessel opened and contacted air for the evaporation of added chloroform. 24 hours later, ultrafiltration was performed for every solution with molecular weight cut-off (MWCO) 1000 filter in order to eliminate remaining adriamycin which didn't permeate into the inside of adriamycin-chitosan complex. The gathered materials on the filter were dissolved in required amount of water again and then freeze-dried, resulting in the preparation of adriamycin-chitosan complex containing adriamycin inside (Table 1). In the Table 1, the loading effect represents the actual amount of loaded adriamycin in adriamycin-chitosan complex by %.

TABLE 1

| Adriamycin-chitosan complex/water (mg/ml) | Adriamycin (mg) | Amount of loading (w/w %) | Loading effect (%) |
|---|---|---|---|
| 5 mg/10 ml | 1 mg | 18.9 W % | 94.33% |
| 5 mg/10 ml | 2 mg | 38.9 W % | 97.23% |

Example 11

Preparation of adriamycin-chitosan Complex Forming Self-Aggregates Containing adriamycin Therein 2

The present inventors dissolved 1 mg of adriamycin in 1 ml chloroform solution. And, the same method as the above Example 10 was performed for the rest of the procedure to prepare adriamycin-chitosan complex forming self-aggregates containing adriamycin therein (Table 1).

Example 12

Preparation of adriamycin-chitosan Complex Forming Self-Aggregates Containing Taxol Therein 1

1 mg of taxol was dissolved in 1 ml DMF in order to prepare adriamycin-chitosan complex containing taxol inside. 5 mg of adriamycin-chitosan complex of the present invention was dissolved in 10 ml of water, and then the above taxol solution was slowly loaded thereto, followed by 24 hours stirring. 24 hours later, dialysis was performed for every solution with a MWCO 3500 membrane for 2 days in order to eliminate remaining taxol which didn't permeate into the inside of adriamycin-chitosan complex. After the dialysis, the solution was freeze-dried, resulting in the preparation of adriamycin-chitosan complex containing taxol therein.

Example 13

Preparation of adriamycin-chitosan Complex Forming Self-Aggregates Containing Taxol Therein 2

The present inventors dissolved 2 mg of taxol in 1 ml of DMF. And, the same method as the above Example 12 was performed for the rest of the procedure to prepare adriamycin-chitosan complex forming self-aggregates containing taxol therein.

Experimental Example 1

Measurement of Released adriamycin from adriamycin-chitosan Complex According to pH The present inventors have observed the releasing level of adriamycin according to the pH from the adriamycin-chitosan complex of the present invention. Particularly, adriamycin-chitosan complex was dispersed into water until the concentration reached at 2 mg/ml, and then 500 µl of adriamycin-chitosan complex solution was enveloped in cellulose dialysis membrane (MWCO 12,000-14,000). After soaking thereof in each pH 4 and pH 7 water, the present inventors stirred thereof at 37° C. with 150 rpm and obtained releasing solution according to the time-table to measure the amount of released adriamycin with a spectrophotometer.

As a result, as shown in FIG. 3, the amount of released adriamycin was gradually increased in both cases of pH 4 and pH 7 as time went by. But when being soaked in pH 4 water solution, the adriamycin-chitosan complex of the present invention released much more adriamycin comparatively, suggesting that the adriamycin-chitosan complex can be effectively used for the treatment of cancer by releasing adriamycin properly to the tumor-growing area which shows generally acidic condition.

INDUSTRIAL APPLICABILITY

As shown above, the anticancer drug-chitosan complex of the present invention has prolonged drug-releasing time by forming self-aggregates, enhanced selectivity against tumor tissues, and increase the amount of drug by adding the anticancer drug into the inside of self-aggregates physically. Therefore, the anticancer drug-chitosan complex of the present invention can be effectively used for cancer chemotherapy.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An anticancer drug-chitosan conjugate comprising:
   an adriamycin; and
   a hydrophilic glycol chitosan,
   wherein the adriamycin is bonded to the glycol chitosan via a linker which degrades in an acidic condition, and
   wherein the conjugate self-aggregates in an aqueous media.

2. The anticancer drug-chitosan conjugate as set forth in claim 1, wherein the content of the adriamycin ranges from 1 to 70 weight %.

3. The anticancer drug-chitosan conjugate as set forth in claim 1, wherein the mean molecular weight of the chitosan is $10^3 \sim 10^6$ dalton.

4. The anticancer drug-chitosan conjugate as set forth in claim 1, wherein the linker is selected from the group consisting of cis-aconitic anhydride, benzoyl hydrazone, and oligopeptide and wherein the adriamycin is bonded to the glycol chitosan via the linker which degrades in an acidic condition.

5. The anticancer drug-chitosan conjugate as set forth in claim 1, wherein the diameter of the self-aggregated complex is 10~800 nm.

6. The anticancer drug-chitosan conjugate as set forth in claim 1, wherein a hydrophobic anticancer drug is further loaded inside the self-aggregates.

7. The anticancer drug-chitosan conjugate as set forth in claim 6, wherein the hydrophobic anticancer drug is selected from the group consisting of adriamycin, taxol, cis-platin, daunomycin and 5-fluorouracil.

* * * * *

UNITED STATES PATENT AND TRADEMARK OFFICE
CERTIFICATE OF CORRECTION

PATENT NO. : 7,511,023 B2
APPLICATION NO. : 10/473629
DATED : March 31, 2009
INVENTOR(S) : Ick Chan Kwon et al.

It is certified that error appears in the above-identified patent and that said Letters Patent is hereby corrected as shown below:

Title Page Item (73) on the Title page of the patent, the second assignee --JAKWANG CO., LTD (KR)-- should be added Signed and Sealed this Sixteenth Day of March, 2010

David J. Kappos
*Director of the United States Patent and Trademark Office*